(12) United States Patent
Mizuguchi et al.

(10) Patent No.: US 11,089,816 B2
(45) Date of Patent: Aug. 17, 2021

(54) POWER SUPPLY UNIT OF AEROSOL GENERATION APPARATUS

(71) Applicant: JAPAN TOBACCO INC., Tokyo (JP)

(72) Inventors: Kazuma Mizuguchi, Tokyo (JP); Manabu Yamada, Tokyo (JP); Ryoji Fujita, Tokyo (JP); Hajime Fujita, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 16/931,447

(22) Filed: Jul. 17, 2020

(65) Prior Publication Data

US 2021/0015163 A1 Jan. 21, 2021

(30) Foreign Application Priority Data

Jul. 17, 2019 (JP) .............................. JP2019-131692

(51) Int. Cl.
*H02J 7/00* (2006.01)
*A24F 40/53* (2020.01)
*A24F 40/485* (2020.01)
*A24F 40/51* (2020.01)
*A61M 15/06* (2006.01)
*H01M 10/0525* (2010.01)
*H01M 10/42* (2006.01)
*H01M 10/48* (2006.01)
(Continued)

(52) U.S. Cl.
CPC ............ *A24F 40/53* (2020.01); *A24F 40/485* (2020.01); *A24F 40/51* (2020.01); *A61M 15/06* (2013.01); *H01M 10/0525* (2013.01); *H01M 10/4228* (2013.01); *H01M 10/48* (2013.01); *H02J 7/0063* (2013.01); *A24F 40/10* (2020.01); *A24F 40/30* (2020.01); *A61M 2205/15* (2013.01); *H01M 2220/30* (2013.01); *H02J 7/02* (2013.01)

(58) Field of Classification Search
None
See application file for complete search history.

(56) References Cited

U.S. PATENT DOCUMENTS

2004/0108861 A1 6/2004 Germiquet et al.
2007/0229294 A1 10/2007 Vossmeyer et al.
(Continued)

FOREIGN PATENT DOCUMENTS

CN 103099319 B 7/2015
CN 104768407 A 7/2015
(Continued)

OTHER PUBLICATIONS

European Search Report dated Nov. 6, 2020, issued in corresponding European Patent Application No. 20186210.9.
(Continued)

*Primary Examiner* — Arun C Williams
(74) *Attorney, Agent, or Firm* — Xsensus LLP

(57) ABSTRACT

A power supply unit of an aerosol generation apparatus includes: a power supply capable of discharging to a load for generating an aerosol from an aerosol source; a controller configured to control the power supply; a housing configured to house the power supply and the controller; and a plurality of sensors capable of outputting the same physical quantity inside the housing. The controller is configured to diagnose a state of the power supply unit based on outputs of the plurality of sensors.

20 Claims, 11 Drawing Sheets

(51) Int. Cl.
*A24F 40/10* (2020.01)
*A24F 40/30* (2020.01)
*H02J 7/02* (2016.01)

(56) References Cited

U.S. PATENT DOCUMENTS

| | | | |
|---|---|---|---|
| 2010/0102975 | A1 | 4/2010 | Vossmeyer et al. |
| 2014/0060554 | A1 | 3/2014 | Collett et al. |
| 2014/0334804 | A1* | 11/2014 | Choi ............... A24F 47/008 392/404 |
| 2014/0366898 | A1* | 12/2014 | Monsees ............ A24F 47/008 131/329 |
| 2015/0027459 | A1 | 1/2015 | Collett et al. |
| 2017/0245547 | A1 | 8/2017 | Lipowicz |
| 2018/0020727 | A1 | 1/2018 | Hoffman et al. |
| 2018/0263290 | A1 | 9/2018 | Collett et al. |
| 2020/0138107 | A1 | 5/2020 | Collett et al. |

FOREIGN PATENT DOCUMENTS

| | | | |
|---|---|---|---|
| CN | 107432498 | A | 12/2017 |
| CN | 207946390 | U | 10/2018 |
| EP | 3 072 406 | A1 | 9/2016 |
| EP | 3 476 645 | A1 | 5/2019 |
| JP | 10-012284 | A | 1/1998 |
| JP | 2002-117911 | A | 4/2002 |
| JP | 2016-536023 | A | 11/2016 |
| JP | 2019-511909 | A | 5/2019 |
| KR | 10-2007-0098691 | A | 10/2007 |
| WO | 2015/035510 | A1 | 3/2015 |
| WO | 2018/142734 | A1 | 8/2018 |
| WO | 2019/064364 | A1 | 4/2019 |

OTHER PUBLICATIONS

Office Action dated Oct. 8, 2020 in Korean Patent Application No. 10-2020-0087271, 13 pages.
Notification of Reasons for Refusal received for Japanese Patent Application No. 2019-131692, dated Oct. 15, 2019, 5 pages including English Translation.
Decision to Grant a Patent received for Japanese Patent Application No. 2019-131692, dated Mar. 3, 2020, 5 pages including English Translation.
Office Action dated May 25, 2021, in corresponding Chinese patent Application No. 202010690468.3, 16 pages.

* cited by examiner

POWER SUPPLY UNIT OF AEROSOL GENERATION APPARATUS

CROSS-REFERENCE TO RELATED APPLICATIONS

This application is based on and claims priority under 35 USC 119 from Japanese Patent Application No. 2019-131692 filed on Jul. 17, 2019, the contents of which are incorporated herein by reference.

TECHNICAL FIELD

The present disclosure relates to a power supply unit of an aerosol generation apparatus.

BACKGROUND ART

Japanese Translation of PCT International Application Publication No. JP-T-2016-536023 (hereinafter, referred to as Patent Literature 1) discloses a personal electronic inhaler including a power supply such as a battery, an atomizer that may include one or a plurality of heating element(s), and a bulkhead for separating a battery from an atomizer region. According to such a personal electronic inhaler, when an electrolytic solution leaks from the battery, the bulkhead can prevent the electrolytic solution from flowing out to an atomizer side.

Description of Chinese Patent Publication No. 103099319 (hereinafter, referred to as Patent Literature 2) discloses a sealing layer that prevents outflow of an electrolytic solution and an adsorption layer that adsorbs the electrolytic solution when the outflow of the electrolytic solution cannot be stopped by the sealing layer.

Description of Chinese Patent Publication No. 107432498 (hereinafter, referred to as Patent Literature 3) discloses an electronic cigarette in which a housing made of aluminum and a plastic film is provided in a housing made of steel in order to prevent an electrolytic solution from flowing out to outside.

However, in Patent Literatures 1 to 3, although a method is disclosed which prevents other components from being influenced when the electrolytic solution leaks from the battery, the leakage of the electrolytic solution from the battery cannot be recognized. In other words, even after the electrolytic solution leaks, an operation of the personal electronic inhaler or the like is continued.

Further, in Patent Literatures 1 to 3, when a liquid enters into the housing due to submersion or the like, the entering of the liquid cannot be recognized. In a power supply unit of an aerosol generation apparatus, it is important to recognize a state that may influence an operation of the aerosol generation apparatus, such as the leakage of the liquid, the entering of the liquid, a bulge of the power supply (cell), and the like.

An object of the present disclosure is to provide a power supply unit of an aerosol generation apparatus that can accurately diagnose a state of the power supply unit.

SUMMARY

A power supply unit of an aerosol generation apparatus of the present disclosure includes: a power supply capable of discharging to a load for generating an aerosol from an aerosol source; a controller configured to control the power supply; a housing configured to house the power supply and the controller; and a plurality of sensors capable of outputting the same physical quantity inside the housing. The controller is configured to diagnose a state of the power supply unit based on outputs of the plurality of sensors.

According to the present disclosure, the influence of at least one of the leakage of the liquid and the entering of the liquid can be avoided.

DESCRIPTION OF EMBODIMENTS

Hereinafter, a power supply unit of an aerosol generation apparatus according to an embodiment of the present disclosure will be described. First, an aerosol suction device on which the power supply unit is mounted will be described with reference to FIGS. 1 to 6.

(Aerosol Suction Device)

Figure 1:
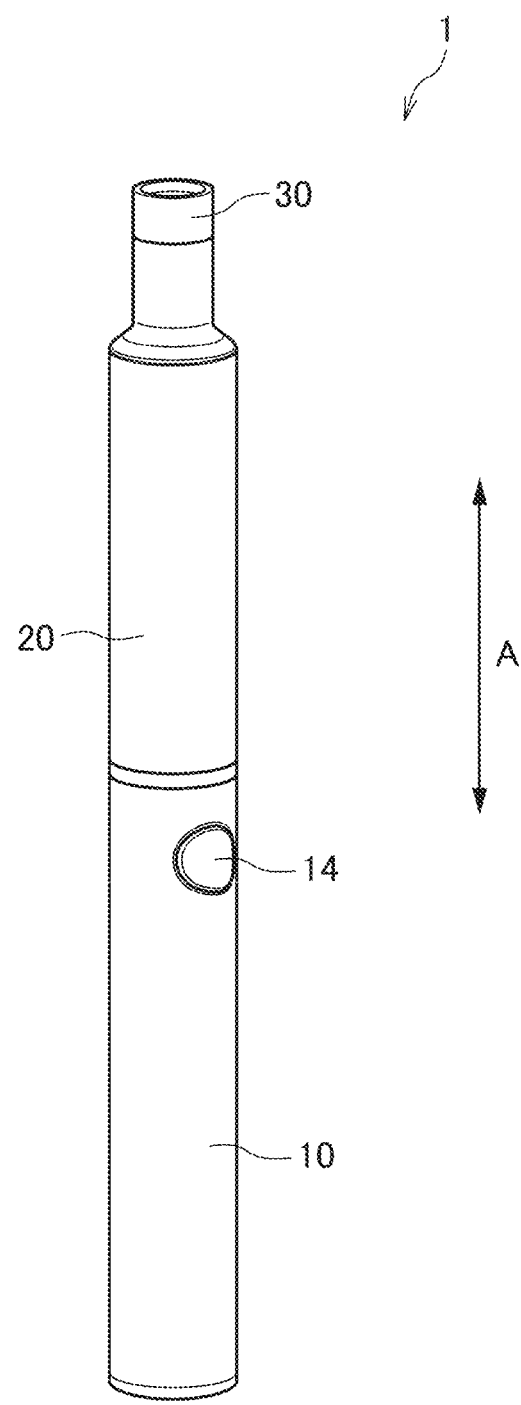
FIG. 1 is a perspective view of an aerosol suction device on which a power supply unit according to an embodiment of the present disclosure is mounted.
Figure 2:
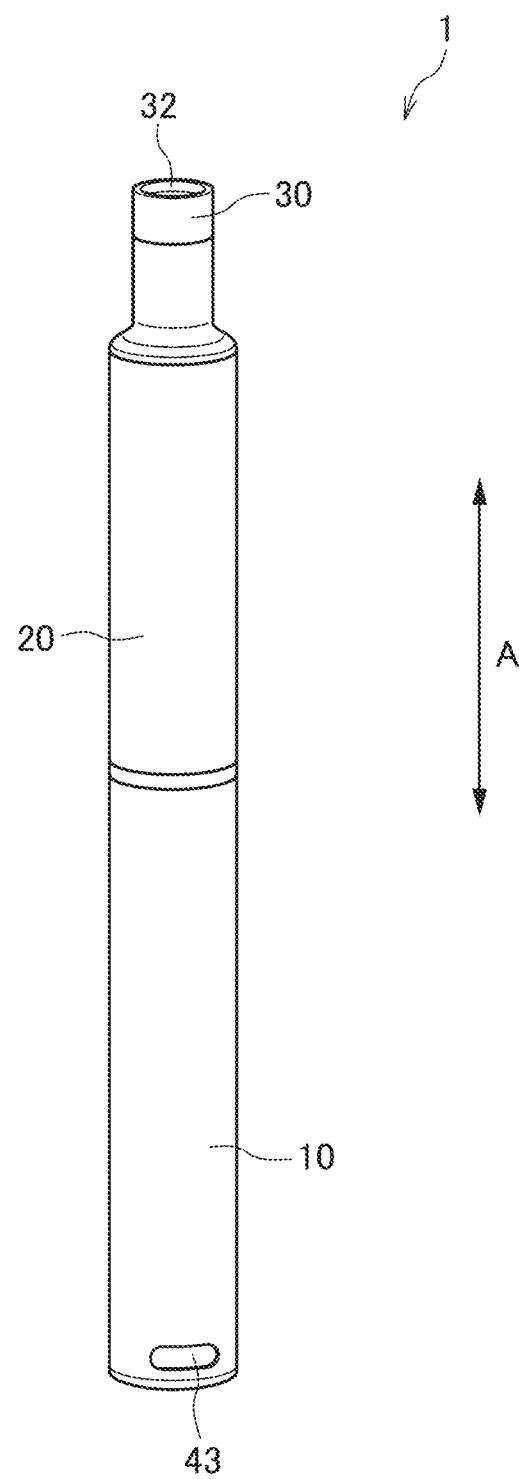
FIG. 2 is another perspective view of the aerosol suction device of FIG. 1.

An aerosol suction device 1 is a device for suctioning a flavor without combustion and has a rod shape that extends along a predetermined direction (hereinafter, referred to as a longitudinal direction A). As shown in FIGS. 1 and 2, the aerosol suction device 1 is provided with a power supply unit 10, a first cartridge 20, and a second cartridge 30 in this order along the longitudinal direction A. The first cartridge 20 is attachable to and detachable from the power supply unit 10, and the second cartridge 30 is attachable to and detachable from the first cartridge 20. In other words, the first cartridge 20 and the second cartridge 30 can be replaced with each other.

(Power Supply Unit)

As shown in FIGS. 3 to 6, the power supply unit 10 of the present embodiment houses a power supply 12, a charger 13, a controller 50, various sensors, and the like inside a cylindrical power supply unit case 11.

The power supply 12 is a rechargeable secondary battery, and preferably a lithium-ion secondary battery. The power supply 12 of the present embodiment includes a cylindrical case 12*a* that houses various components such as an electrode and an electrolytic solution (not shown). A pair of tabs 12*b* (see FIG. 8) serving as positive and negative electrodes are provided at one end portion or both end portions of the power supply 12 in a length direction (longitudinal direction A). In other words, the positive electrode tab 12*b* may be provided on one end of both ends of the power supply 12 in the length direction, and the positive electrode tab 12*b* may be provided on the other end of both ends of the power supply 12 in the length direction. Alternatively, both the positive electrode tab 12*b* and the negative electrode tab 12*b* may be provided on one end of the power supply 12 in the length direction. Further, the power supply 12 includes a safety valve (not shown) that opens when an internal pressure of the power supply 12 is larger than a predetermined pressure, on one end portion or both end portions in the length direction.

A discharge terminal 41 is provided on a top portion 11*a* positioned on one end side (first cartridge 20 side) of the power supply unit case 11 in the longitudinal direction A. The discharge terminal 41 protrudes from an upper surface of the top portion 11*a* toward the first cartridge 20 and can be electrically connected to a load 21 of the first cartridge 20.

An air supply portion 42 that supplies air to the load 21 of the first cartridge 20 is provided in the vicinity of the discharge terminal 41 on the upper surface of the top portion 11*a*.

A charging terminal 43 that can be electrically connected to an external power supply 60 (see FIG. 5) that can charge the power supply 12 is provided inside a bottom portion 11*b* positioned on the other end side (side opposite to the first cartridge 20) of the power supply unit case 11 in the longitudinal direction A. The charging terminal 43 is provided inside a side surface of the bottom portion 11*b*, and at least one of a USB terminal, a microUSB terminal, and a Lightning (registered trademark) terminal can be connected to the charging terminal 43.

The charging terminal 43 may be a power receiving unit that can receive, in a wireless manner, power supplied from the external power supply 60. In such a case, the charging terminal 43 (power receiving unit) may be configured with a power receiving coil. A method for the wireless power transfer may be electromagnetic induction or magnetic resonance. Further, the charging terminal 43 may be a power receiving unit that can receive, without contact, the power supplied from the external power supply 60. As another example, at least one of the USB terminal, the microUSB terminal, and the Lightning (registered trademark) terminal can be connected to the charging terminal 43, and the charging terminal 43 may include the above-described power receiving unit.

That is, in the power supply unit 10, the discharge terminal 41 and the charging terminal 43 are separately configured and arranged apart from each other in the longitudinal direction A. Therefore, the power supply unit 10 is configured such that the external power supply 60 can be electrically connected to the charging terminal 43 in a state where the power supply 12 can be discharged via the discharge terminal 41. Further, in the power supply unit 10, when an aerosol generation request is detected while the charging terminal 43 and the external power supply 60 are electrically connected, simultaneous charging and discharging of the power supply 12 is prohibited.

The power supply unit case 11 is provided with an operation unit 14 that can be operated by a user, on a side surface of the top portion 11*a*, so as to face a side opposite to the charging terminal 43. More specifically, the operation unit 14 and the charging terminal 43 are in a point-symmetrical relationship with an intersection of a straight line that connects the operation unit 14 to the charging terminal 43 and a center line L of the power supply unit 10 in the longitudinal direction A. The operation unit 14 is configured with a button type switch, a touch panel, and the like and is used when a use intention of the user is reflected so as to activate/interrupt the controller 50 and various sensors. The controller 50 and an intake sensor 15 that detects a puff operation are provided in the vicinity of the operation unit 14.

The charger 13 controls charging power input from the charging terminal 43 to the power supply 12. The charger 13 is configured by using a charging IC that is mounted on a charging cable connected to the charging terminal 43 and that includes a converter that converts a direct current from an inverter 61 or the like into a direct current having different magnitude, a voltmeter, an ammeter, a processor, and the like. The inverter 61 or the like converts an alternating current into a direct current.

Figure 6:
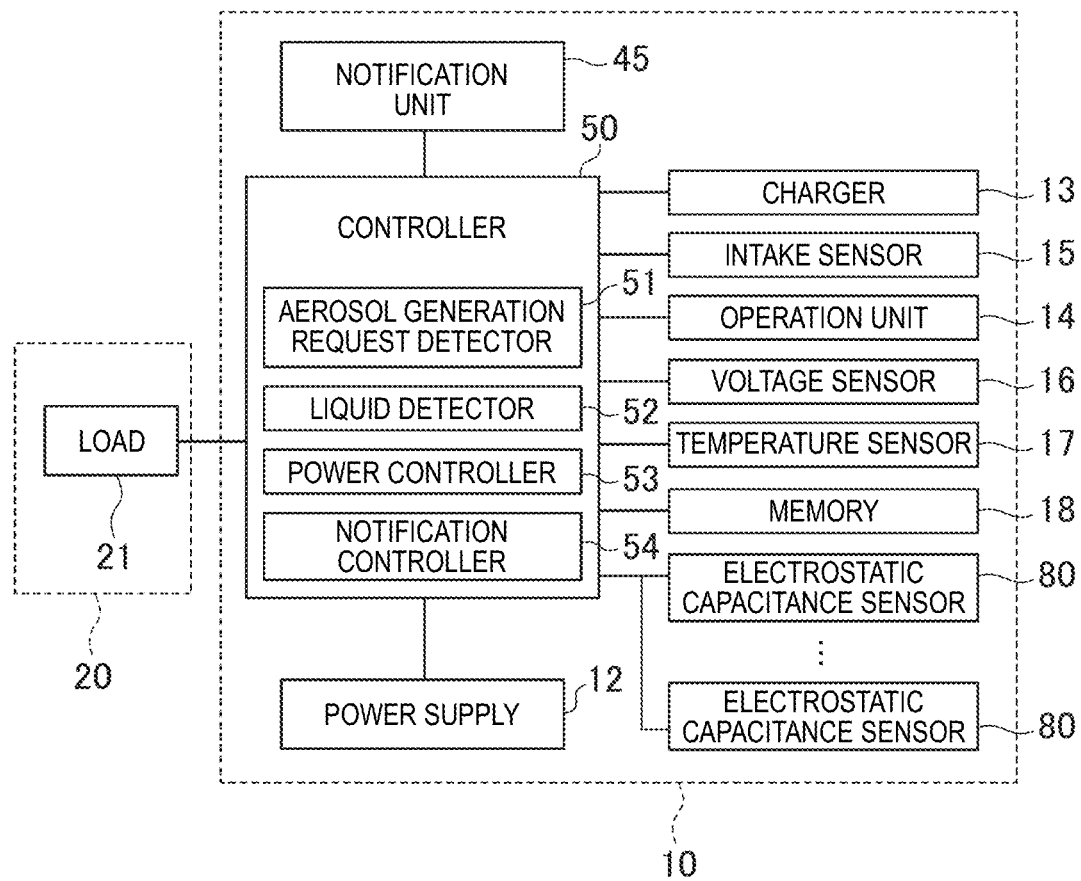
FIG. 6 is a block diagram showing a configuration of main parts of the power supply unit in the aerosol suction device of FIG. 1.

As shown in FIG. 6, the controller 50 is connected to the charger 13, the operation unit 14, various sensor devices such as the intake sensor 15 that detects the puff (intake) operation, a voltage sensor 16 that measures a voltage of the power supply 12, a temperature sensor 17 that detects a temperature, an electrostatic capacitance sensor 80 that is separate from the intake sensor 15 and detects electrostatic capacitance inside the power supply unit case 11, and a memory 18 that stores the number of puff operations, time for energizing the load 21, or the like, and performs various controls of the aerosol suction device 1. The intake sensor 15 may be configured with a condenser microphone, a pressure sensor, or the like. Specifically, the controller 50 is a processor (MCU: Micro Controller Unit). More specifically, the structure of the processor is an electric circuit in which circuit elements such as semiconductor elements are combined. Details of the controller 50 will be described later.

The power supply unit case 11 is provided with an air intake port 11*c* that takes outside air into inside thereof. The air intake port 11*c* may be provided around the operation unit 14 or may be provided around the charging terminal 43.

(First Cartridge)

Figure 3:
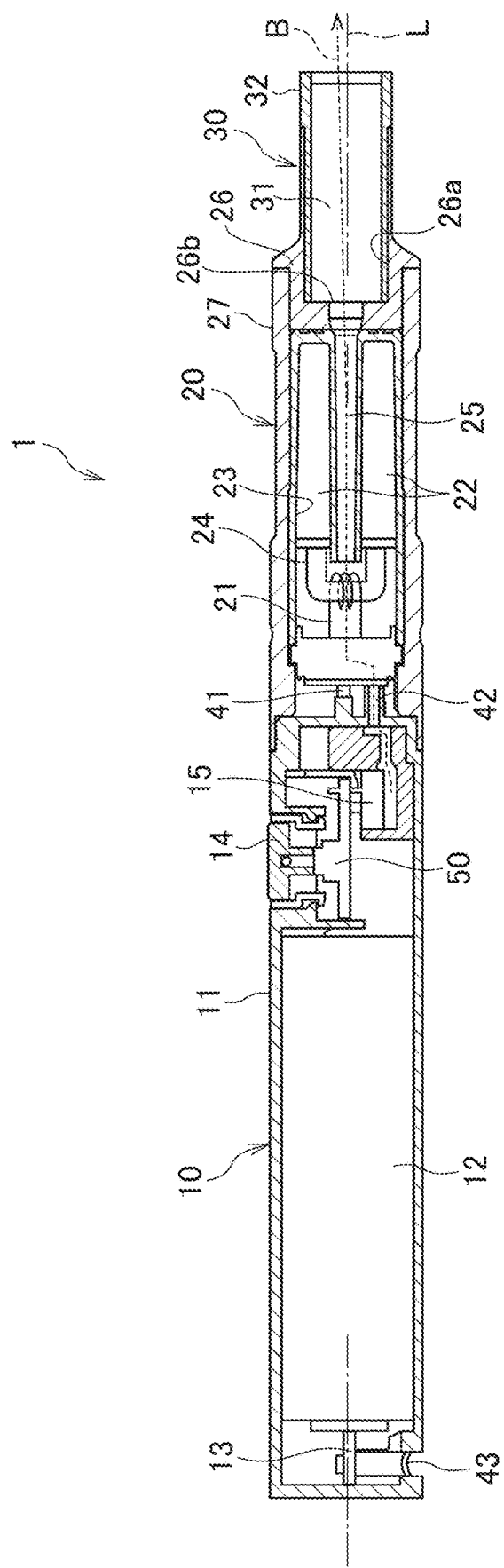
FIG. 3 is a cross-sectional view of the aerosol suction device of FIG. 1.

As shown in FIG. 3, the first cartridge 20 includes, inside a cylindrical cartridge case 27, a reservoir 23 that stores an aerosol source 22, the electrical load 21 that atomizes the aerosol source 22, a wick 24 that draws the aerosol source from the reservoir 23 into the load 21, an aerosol flow path 25 that causes an aerosol generated by the atomization of the aerosol source 22 to flow toward the second cartridge 30, and an end cap 26 that houses a part of the second cartridge 30.

The reservoir 23 is partitioned and formed so as to surround a periphery of the aerosol flow path 25 and stores the aerosol source 22. A porous body such as a resin web or cotton may be housed in the reservoir 23, and the aerosol source 22 may be impregnated in the porous body. In the reservoir 23, the porous body on the resin web or the cotton may not be housed and only the aerosol source 22 may be stored. The aerosol source 22 contains liquids such as glycerin, propylene glycol, and water.

The wick 24 is a liquid holding member that draws the aerosol source 22 from the reservoir 23 into the load 21 by using a capillary phenomenon, and is configured with, for example, glass fiber or porous ceramic.

The load 21 atomizes the aerosol source 22 without combustion by power supplied from the power supply 12 via the discharge terminal 41. The load 21 is configured with an electric heating wire (coil) wound at a predetermined pitch. The load 21 may be an element that can atomize the aerosol source 22 so as to generate an aerosol, and is, for example, a heating element or an ultrasonic generator. Examples of the heating element include a heating resistor, a ceramic heater, and an induction heating heater.

The aerosol flow path 25 is downstream of the load 21 and provided on the center line L of the power supply unit 10.

The end cap 26 includes a cartridge housing portion 26a that houses a part of the second cartridge 30, and a communication path 26b that communicates the aerosol flow path 25 with the cartridge housing portion 26a.

(Second Cartridge)

The second cartridge 30 stores a flavor source 31. The second cartridge 30 is detachably housed in the cartridge housing portion 26a provided in the end cap 26 of the first cartridge 20. An end portion of the second cartridge 30 on a side opposite to a first cartridge 20 side is a suction port 32 of the user. The suction port 32 is not limited to the case of being integrally formed with the second cartridge 30 and may be configured to be attachable to and detachable from the second cartridge 30. Accordingly, the suction port 32 is separate from the power supply unit 10 and the first cartridge 20, so that the suction port 32 can be kept hygienic.

The second cartridge 30 causes an aerosol generated by atomizing the aerosol source 22 by the load 21 to pass through the flavor source 31, so that a flavor is given to the aerosol. As a raw material piece that constitutes the flavor source 31, a molded body obtained by molding shredded tobacco or a tobacco raw material into a granular shape can be used. The flavor source 31 may be configured with a plant other than tobacco (for example, mint, Chinese herbs, herbs, or the like). A flavor material such as menthol may be given to the flavor source 31.

In the aerosol suction device 1 of the present embodiment, the aerosol source 22, the flavor source 31, and the load 21 can generate an aerosol to which a flavor is added. That is, the aerosol source 22 and the flavor source 31 can be referred to as an aerosol generation source that generates an aerosol.

In addition to the configuration in which the aerosol source 22 and the flavor source 31 are separated from each other, the configuration of the aerosol generation source used in the aerosol suction device 1 may be a configuration in which the aerosol source 22 and the flavor source 31 are integrally formed, a configuration in which the flavor source 31 is omitted and a substance that may be contained in the flavor source 31 is added to the aerosol source 22, a configuration in which a medication or the like is added to the aerosol source 22 instead of the flavor source 31, or the like.

In the aerosol suction device 1 configured as described above, as indicated by an arrow B in FIG. 3, air that flows in from the air intake port 11c provided in the power supply unit case 11 passes near the load 21 of the first cartridge 20 from the air supply portion 42. The load 21 atomizes the aerosol source 22 drawn or moved from the reservoir 23 by the wick 24. An aerosol generated by the atomization flows through the aerosol flow path 25 together with air that flows in from the air intake port 11c, and is supplied to the second cartridge 30 via the communication path 26b. The aerosol supplied to the second cartridge 30 is given a flavor by passing through the flavor source 31 and is supplied to the suction port 32.

The aerosol suction device 1 is provided with a notification unit 45 that notifies various pieces of information. The notification unit 45 may be configured with a light-emitting element, may be configured with a vibration element, or may be configured with a sound output element. Further, the notification unit 45 may be a combination of two or more elements among the light-emitting element, the vibration element, and the sound output element. The notification unit 45 may be provided in any of the power supply unit 10, the first cartridge 20, and the second cartridge 30, and is preferably provided in the power supply unit 10 in order to shorten a conductive wire from the power supply 12. For example, a periphery of the operation unit 14 is translucent. The notification unit 45 emits light by a light-emitting element such as an LED.

(Electric Circuit)

Next, an electric circuit of the power supply unit 10 will be described with reference to FIG. 5.

The power supply unit 10 includes the power supply 12, a positive electrode side discharge terminal 41a and a negative electrode side discharge terminal 41b that constitute the discharge terminal 41, a positive electrode side charging terminal 43a and a negative electrode side charging terminal 43b that constitute the charging terminal 43, the controller 50 connected between a positive electrode side of the power supply 12 and the positive electrode side discharge terminal 41a and between a negative electrode side of the power supply 12 and the negative electrode side discharge terminal 41b, the charger 13 disposed on a power transmission path between the charging terminal 43 and the power supply 12, the voltage sensor 16 connected in parallel with the power supply 12, a switch 19 disposed on a power transmission path between the power supply 12 and the discharge terminal 41, and plural electrostatic capacitance sensors 80 connected to the controller 50. The switch 19 is configured with, for example, a MOSFET, and is opened and closed by the controller 50 adjusting a gate voltage.

(Controller)

As shown in FIG. 6, the controller 50 includes an aerosol generation request detector 51, a liquid detector 52, a power controller 53, and a notification controller 54.

The aerosol generation request detector 51 detects an aerosol generation request based on an output result of the intake sensor 15. The intake sensor 15 outputs a value of a pressure change in the power supply unit 10 caused by suction of the user through the suction port 32. The intake sensor 15 is, for example, a pressure sensor that outputs an output value (for example, a voltage value or a current value) corresponding to an atmospheric pressure that changes in accordance with a flow rate of air suctioned from the air intake port 11c toward the suction port 32 (that is, a puff operation of the user).

Based on an output of the electrostatic capacitance sensor 80, the liquid detector 52 detects leakage of a liquid inside the power supply unit case 11 (hereinafter, referred to as liquid leakage detection), or detects entering of the liquid into the power supply unit case 11 (hereinafter, referred to as liquid entering detection). Further, the liquid detector 52 prohibits charging/discharging of the power supply 12 in accordance with a detection result. According to such a liquid detector 52, it is possible to avoid an influence of the leakage of the liquid, the entering of the liquid, or the like on an operation of the aerosol suction device 1. Further, the electrostatic capacitance sensor 80 is used, so that the leakage of the liquid and the entering of the liquid can be accurately detected with an inexpensive configuration. A specific processing procedure of the liquid detector 52 will be described later.

The notification controller 54 controls the notification unit 45 so as to notify various pieces of information. For example, the notification controller 54 controls the notification unit 45 so as to notify a replacement timing of the second cartridge 30 in response to detection of the replacement timing of the second cartridge 30. The notification controller 54 notifies the replacement timing of the second cartridge 30 based on the number of puff operations or accumulated energization time for the load 21 that are stored in the memory 18. The notification controller 54 is not limited to the notification of the replacement timing of the second cartridge 30, and may notify a replacement timing of the first cartridge 20, a replacement timing of the power supply 12, a charging timing of the power supply 12, and the like.

The power controller 53 controls discharge of the power supply 12 via the discharge terminal 41 by turning ON/OFF the switch 19 when the aerosol generation request detector 51 detects an aerosol generation request.

The power controller 53 performs control such that an amount of an aerosol generated by the load 21 atomizing the aerosol source falls within a desired range, in other words, performs control such that an amount of power supplied from the power supply 12 to the load 21 falls within a certain range. Specifically, the power controller 53 controls ON/OFF of the switch 19 by, for example, pulse width modulation (PWM) control. Instead, the power controller 53 may control ON/OFF of the switch 19 by pulse frequency modulation (PFM) control.

The power controller 53 may stop power supply from the power supply 12 to the load 21 when a predetermined period has elapsed after the power supply to the load 21 is started. In other words, the power controller 53 stops the power supply from the power supply 12 to the load 21 when a puff period exceeds a predetermined period even within the puff period during which the user actually performs the puff operation. The predetermined period is determined in order to prevent a variation in the puff period of the user. The power controller 53 controls an ON/OFF duty ratio of the switch 19 in a single puff operation in accordance with a power storage amount of the power supply 12. For example, the power controller 53 controls an on-time interval (pulse interval) for supplying power from the power supply 12 to the load 21, or controls an on-time length (pulse width) for supplying power from the power supply 12 to the load 21.

The power controller 53 detects an electrical connection between the charging terminal 43 and the external power supply 60 and controls charging of the power supply 12 via the charger 13.

(Board Configuration)

Figure 7:
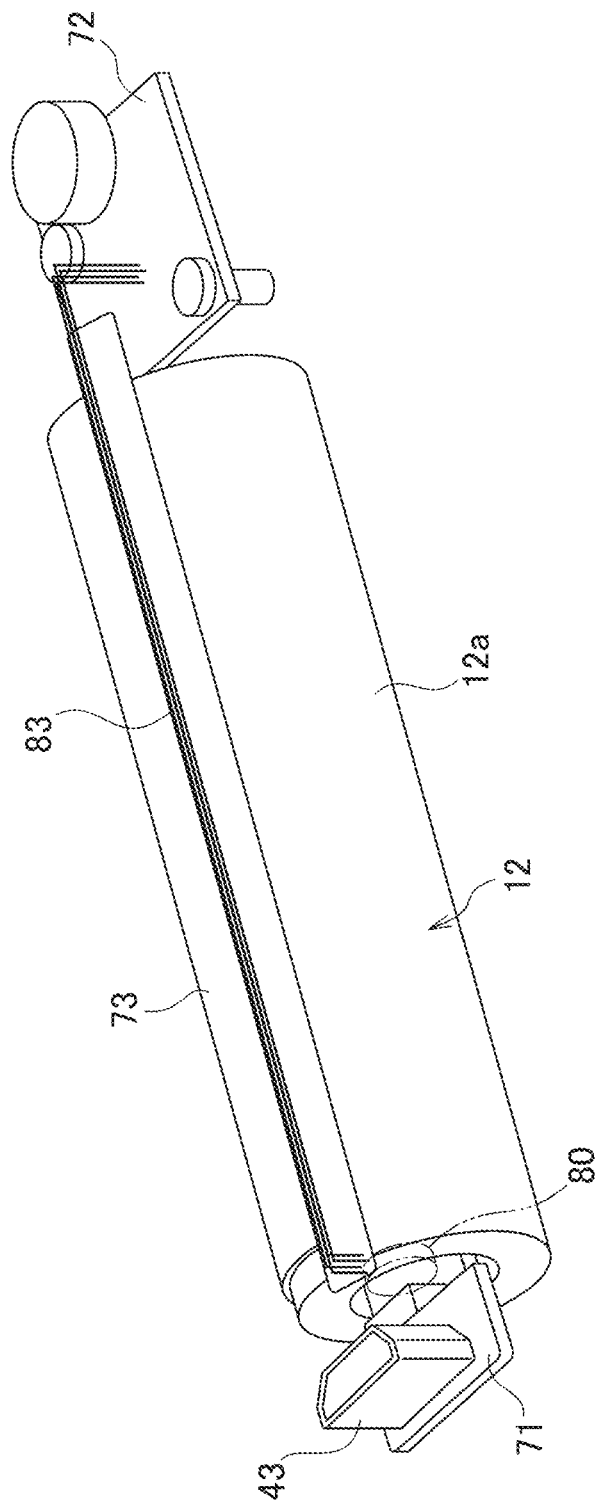
FIG. 7 is a perspective view of main parts showing a board configuration of the power supply unit in the aerosol suction device of FIG. 1.

As shown in FIG. 7, the power supply unit 10 includes a first circuit board 71 provided with the charging terminal 43 and the like, a second circuit board 72 provided with the controller 50, the charger 13, the switch 19 and the like, and a conductive member 73 that electrically connects the first circuit board 71 to the second circuit board 72. The conductive member 73 of the present embodiment is configured using a flexible printed circuit board (FPCB), but may be configured with a conductive wire.

The first circuit board 71 and the second circuit board 72 are arranged apart from each other. Specifically, the first circuit board 71 is provided on one end side in the length direction of the power supply 12 (longitudinal direction A), the second circuit board 72 is provided on the other end side in the length direction of the power supply 12 (longitudinal direction A), and the first circuit board 71 and the second circuit board 72 are electrically connected to each other via the conductive member 73 that extends in the length direction of the power supply 12 along a peripheral surface of the power supply 12.

(Liquid Leakage Detection)

Next, the liquid leakage detection by the controller 50 (liquid detector 52) will be described with reference to FIGS. 7 and 8. In the present embodiment, an electrolytic solution of the power supply 12 is assumed as a liquid leaked inside the power supply unit case 11. It should be noted that in the following description, the term "electrolytic solution" may indicate either an ionic liquid or a flame retardant organic solvent.

The power supply 12 may include an electrolyte other than an electrolytic solution. As an example, the power supply 12 may include both a solid or gel-shaped solid electrolyte and an electrolytic solution. Further, the electrolytic solution may be a mixed solution containing a plurality of liquids. Further, a lithium salt or the like for improving performance of the power supply 12 may be added as an additive to the electrolytic solution.

The electrostatic capacitance sensor 80 is a sensor that detects an object, a fluid, or the like based on a change in an electrostatic capacitance that occurs between a sensor electrode 81 and a GND potential, and detects the electrolytic solution leaked from the power supply 12 in the present embodiment. The electrostatic capacitance sensor 80 of the present embodiment constitutes, between the electrode 81 and the GND potential, a pseudo capacitor by sandwiching a first porous body 82 that absorbs the electrolytic solution so as to guide the electrolytic solution to the electrode 81, and measures an electrostatic capacitance of the capacitor by the controller 50. For example, the controller 50 charges and discharges the capacitor including the electrostatic capacitance sensor 80, and measures an electrostatic capacitance based on a time required for the charging and discharging. According to such an electrostatic capacitance sensor 80, when the first porous body 82 absorbs the electrolytic solution, an electrostatic capacitance is changed. Therefore, the controller 50 can accurately detect the electrolytic solution leaked from the power supply 12. Further, since the electrode 81 can be configured with a metal plate and the first porous body 82 can be configured with a cotton sheet, a sponge, absorbent cotton, or the like, the electrolytic solution leakage of the power supply 12 can be detected with an inexpensive configuration. The electrode 81 and the first porous body 82 may be unitized so as to form an electrostatic capacitance sensor unit. Instead of the pseudo capacitor including only one electrode 81, the electrostatic capacitance sensor 80 may be configured with a capacitor including two facing electrodes 81.

It is desirable that the electrostatic capacitance sensor 80 is disposed in the power supply 12 at a location where the electrolytic solution leaks easily. Generally, in the power supply 12, the electrolytic solution leakage easily occurs in the vicinity of the tab 12b and the safety valve. Therefore, it is desirable that at least a part of the first porous body 82 is disposed so as to abut against the tab 12b and the safety valve or is disposed in the vicinity of the tab 12b and the safety valve. Accordingly, when the electrolytic solution leakage occurs in the vicinity of the tab 12b and the safety valve of the power supply 12, the electrolytic solution leakage can be effectively and rapidly detected. At least a part of the first porous body 82 being disposed so as to abut against the tab 12b and the safety valve obviously means that the entire first porous body 82 abuts against the tab 12b and the safety valve, and means that a part of the first porous body 82 (for example, arm portion) extends toward the tab 12b and the safety valve and abuts against the tab 12b and the safety valve while the first porous body 82 is separated from the tab 12b and the safety valve. Further, at least a part of the first porous body 82 being disposed in the vicinity of the tab 12b and the safety valve obviously means that the entire first porous body 82 is positioned in the vicinity of the tab 12b and the safety valve, and means that a part of the first porous body 82 (for example, arm portion) is positioned in the vicinity of the tab 12b and the safety valve while the first porous body 82 is separated from the tab 12b and the safety valve. The vicinity is a position including at least a position that can be in contact with an electrolytic solution when the electrolytic solution leaks.

As shown in FIG. 7, when the electrostatic capacitance sensor 80 is disposed on one end side of the power supply 12 and the controller 50 (second circuit board 72) is disposed on the other end side of the power supply 12, it is desirable to incorporate the conductive wire 83 that connects the electrostatic capacitance sensor 80 to the controller 50 into the conductive member 73 that is a flexible printed circuit board. Accordingly, wiring of the power supply unit 10 can be saved.

In a case of the power supply unit 10 including a power supply holder (not shown) that is disposed inside the power supply unit case 11 and holds the power supply 12, it is desirable that at least a part of the first porous body 82 is disposed between the power supply 12 and the power supply holder. As a result of intensive studies by the inventors of the present application, it has been found that the power supply holder generates an inevitable gap with the power supply 12 and the electrolytic solution easily enters the gap. Accordingly, even when the electrolytic solution leaks between the power supply 12 and the power supply holder, the electrolytic solution leakage can be detected. In addition to the first porous body 82, the electrostatic capacitance sensor 80 may be disposed between the power supply 12 and the power supply holder. The power supply holder may be electrically conductive or non-conductive.

It is preferable that an electrostatic capacitance of the electrostatic capacitance sensor 80 is changed, based on the electrolytic solution absorbed by the first porous body 82, with a significant difference. Further, it is preferable that the first porous body 82 rapidly transports the absorbed electrolytic solution to a location where the electrostatic capacitance of the electrostatic capacitance sensor 80 is changed. Under such a background, physical properties such as a size of the first porous body 82 are preferably limited. As a result, the first porous body 82 may not be able to absorb the electrolytic solution depending on an amount of the leaked electrolytic solution. It should be noted that the electrolytic solution that cannot be absorbed by the first porous body 82 includes one that cannot be completely absorbed while being once in contact with the first porous body 82 and one that cannot be in contact with the first porous body 82.

Figure 8:
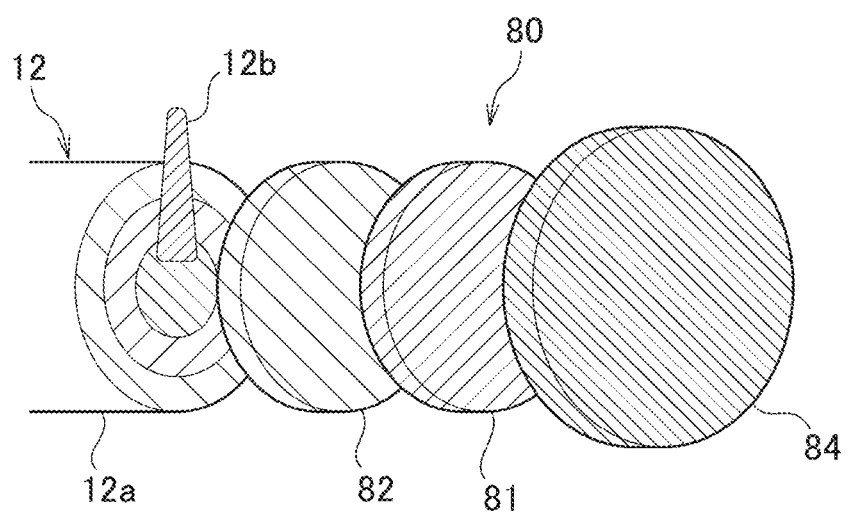
FIG. 8 is an illustrative diagram illustrating an electrostatic capacitance sensor of the power supply unit in the aerosol suction device of FIG. 1.

Therefore, as shown in FIGS. 7 and 8, when the electrostatic capacitance sensor 80 is disposed in the vicinity of the circuit boards 71 and 72, it is desirable to provide a second porous body 84 between the electrostatic capacitance sensor 80 (electrode 81) and the circuit boards 71 and 72. Accordingly, the second porous body 84 can absorb the electrolytic solution that cannot be absorbed by the first porous body 82. As a result, the circuit boards 71 and 72 can be protected from the electrolytic solution that cannot be absorbed by the first porous body 82.

(Liquid Entering Detection)

Next, the liquid entering detection by the controller 50 (liquid detector 52) will be described. In the present embodiment, a liquid that enters into the power supply unit case 11 is assumed to be water that enters during submersion. A structure of the electrostatic capacitance sensor 80 used for the liquid entering detection is substantially the same as the structure of the electrostatic capacitance sensor 80 used for the liquid leakage detection. It is preferable that the electrostatic capacitance sensor 80 used for the liquid entering detection also preferably includes both the first porous body 82 and the second porous body 84.

The controller 50 detects, based on the output of the electrostatic capacitance sensor 80, entering of water from openings K1 to K5 provided in the power supply unit case 11. For example, it is desirable that at least a part of the first porous body 82 that guides water toward the electrode 81 of the electrostatic capacitance sensor 80 is disposed so as to abut against the openings K1 to K5 or is disposed in the vicinity of the openings K1 to K5. Accordingly, entering of water can be effectively detected when the water enters from the openings K1 to K5. At least a part of the first porous body 82 being disposed so as to abut against the openings K1 to K5 obviously means that the entire first porous body 82 abuts against the openings K1 to K5, and means that a part of the first porous body 82 (for example, arm portion) extends toward the openings K1 to K5 and abuts against the openings K1 to K5 while the first porous body 82 is separated from the openings K1 to K5. Further, at least a part of the first porous body 82 being disposed in the vicinity of the openings K1 to K5 obviously means that the entire first porous body 82 is positioned in the vicinity of the openings K1 to K5, and means that a part of the first porous body 82 (for example, arm portion) is positioned in the vicinity of the openings K1 to K5 while the first porous body 82 is separated from the openings K1 to K5. The vicinity is a position that can be in contact with water when the water enters.

In a case where the entire first porous body 82 is disposed so as to abut against the openings K1 to K5 or is disposed in the vicinity of the openings K1 to K5, when submersion occurs, the electrostatic capacitance of the electrostatic capacitance sensor 80 is rapidly changed, so that the submersion can be rapidly detected. When a part of the first porous body 82 extends toward the openings K1 to K5 and abuts against the openings K1 to K5 while the first porous body 82 is separated from the openings K1 to K5, or a part of the first porous body 82 is positioned in the vicinity of the openings K1 to K5, since the electrostatic capacitance sensor 80 can be disposed apart from the openings K1 to K5, a degree of freedom in disposing an electronic component in the power supply unit case 11 is improved. As a result, the power supply unit 10 can be downsized.

Figure 4:
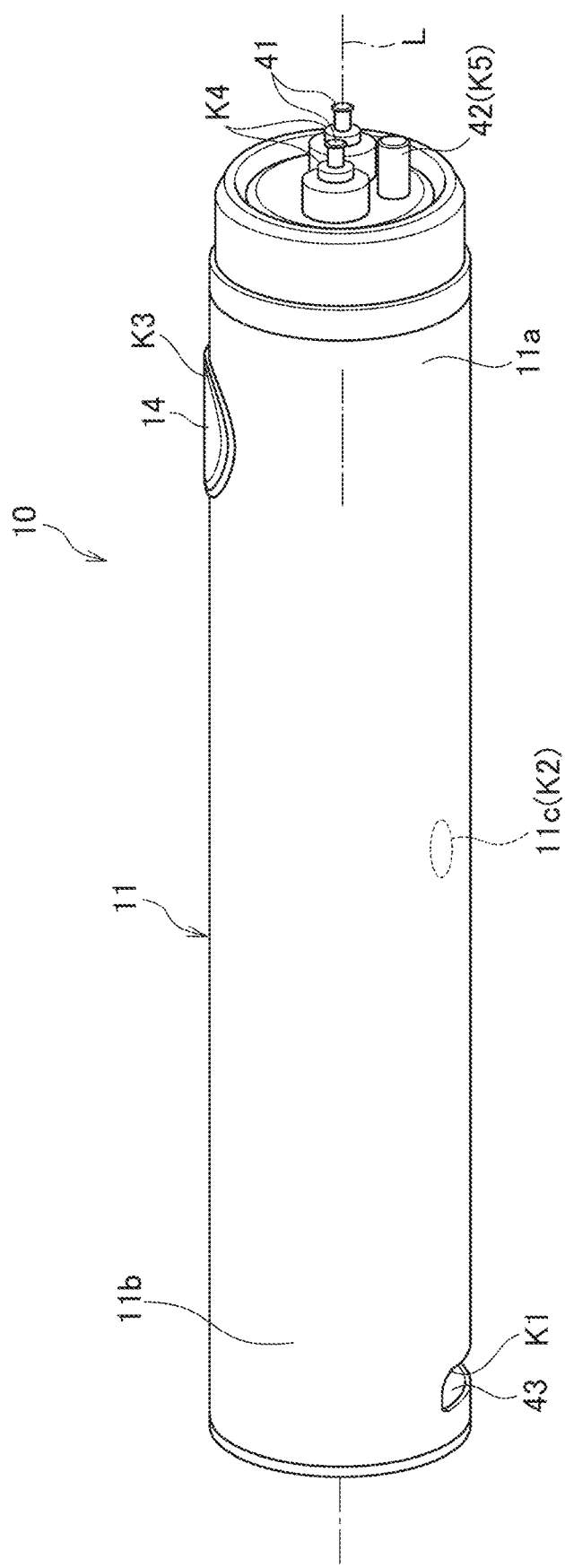
FIG. 4 is a perspective view of the power supply unit in the aerosol suction device of FIG. 1.

As shown in FIG. 4, the opening K1 is formed in the power supply unit case 11 and around the charging terminal 43. When the electrostatic capacitance sensor 80 is disposed in the vicinity of the opening K1 in the power supply unit case 11, entering of water from around the charging terminal 43 can be detected. Further, an influence of the entering of the water on the operation of the aerosol suction device 1 can be avoided.

The opening K2 is the air intake port 11c. When the electrostatic capacitance sensor 80 is disposed in the vicinity of the opening K2 in the power supply unit case 11, entering of water from the air intake port 11c can be detected. Further, an influence of the entering of the water on the operation of the aerosol suction device 1 can be avoided.

The opening K3 is formed in the power supply unit case 11 and around the operation unit 14. When the electrostatic capacitance sensor 80 is disposed in the vicinity of the opening K3 in the power supply unit case 11, entering of water from around the operation unit 14 can be detected. Further, an influence of the entering of the water on the operation of the aerosol suction device 1 can be avoided.

The opening K4 is formed in the power supply unit case 11 and around the discharge terminal 41. When the electrostatic capacitance sensor 80 is disposed in the vicinity of the opening K4 in the power supply unit case 11, entering of water from around the discharge terminal 41 can be detected. Further, an influence of the entering of the water on the operation of the aerosol suction device 1 can be avoided.

The opening K5 is the air supply portion 42. When the electrostatic capacitance sensor 80 is disposed in the vicinity of the opening K5 in the power supply unit case 11, entering of water from the air supply portion 42 can be detected. Further, an influence of the entering of the water on the operation of the aerosol suction device 1 can be avoided.

Among the openings K1 to K5, the opening K2 and the opening K5 are positively provided in the power supply unit case 11 as air flow paths. Therefore, the opening K2 and the opening K5 themselves may become water entering paths. On the other hand, the openings K1, K3, and K4 are provided for assembling separate components to the power supply unit case 11. Therefore, to be precise, in the openings K1, K3, and K4, buffers for absorbing product tolerances of the components to be assembled to the power supply unit case 11 may become water entering paths.

The electrostatic capacitance sensors 80 are arranged at both a location where the electrolytic solution easily leaks and a location where the water easily enters, so that both the liquid leakage detection and the liquid entering detection can be performed. Both the liquid leakage detection and the liquid entering detection are performed, so that safety of the power supply unit 10 and the aerosol suction device 1 can be improved.

(A Plurality of Electrostatic Capacitance Sensors)

Figure 5:
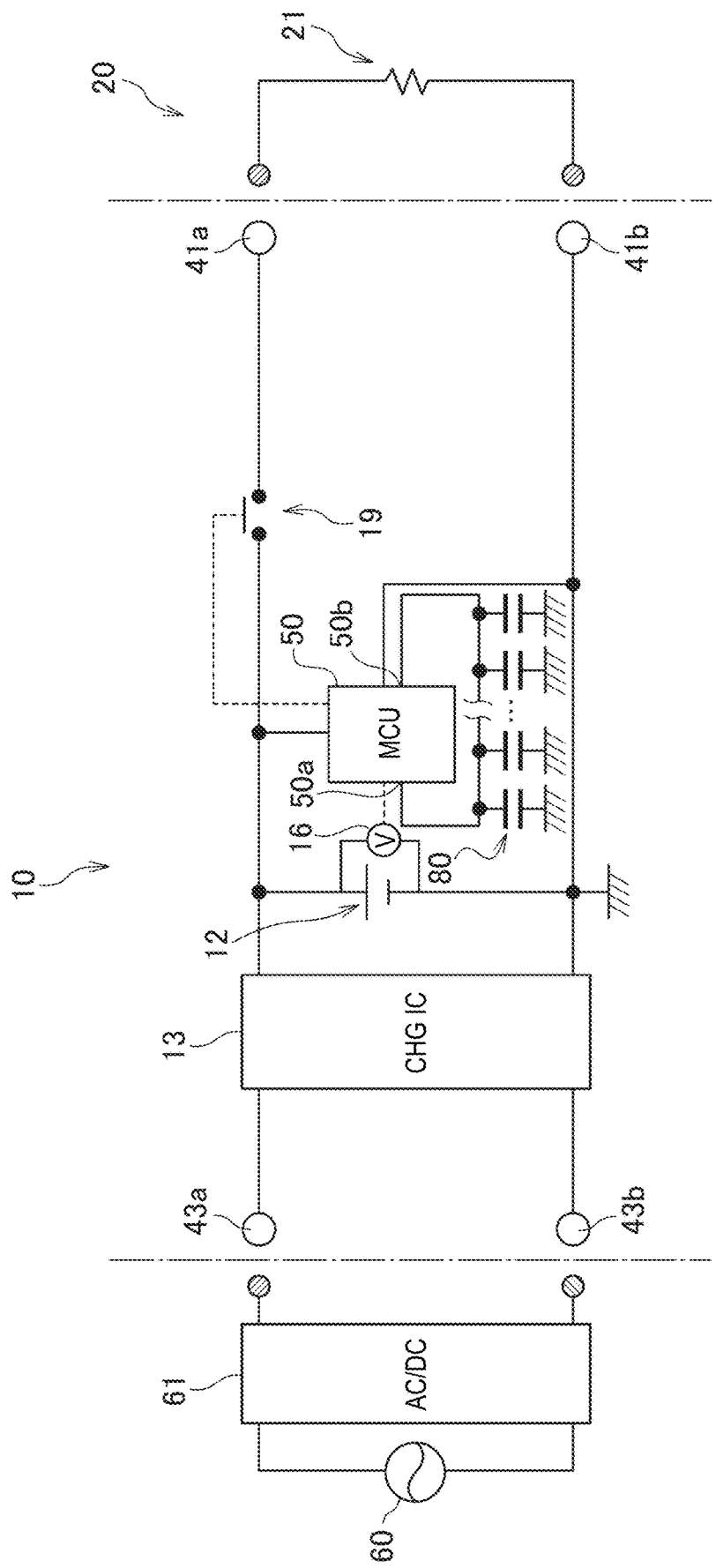
FIG. 5 is a schematic diagram showing a circuit configuration of the power supply unit in the aerosol suction device of FIG. 1.

As shown in FIGS. 5 and 6, the power supply unit 10 includes a plurality of electrostatic capacitance sensors 80. The controller 50 (liquid detector 52) diagnoses a state of the power supply unit 10 (leakage of a liquid or entering of a liquid) based on outputs of the plurality of electrostatic capacitance sensors 80. Accordingly, the state of the power supply unit 10 can be accurately diagnosed as compared with a case where the state of the power supply unit 10 is diagnosed based on an output of one electrostatic capacitance sensor 80. Hereinafter, a method for detecting the leakage of the liquid or the entering of the liquid by using the plurality of electrostatic capacitance sensors 80 will be described in detail.

As shown in FIG. 5, the plurality of electrostatic capacitance sensors 80 are connected in parallel to each other. Accordingly, wiring for connecting the plurality of electrostatic capacitance sensors 80 and the controller 50 can be simplified. At the same time, the wiring for connecting the plurality of electrostatic capacitance sensors 80 and the controller 50 can be reduced. Further, when the plurality of electrostatic capacitance sensors 80 are connected in parallel, the controller 50 can diagnose the state of the power supply unit 10 based on a sum of capacitances that are output values of the plurality of electrostatic capacitance sensors 80. Therefore, even when the number of electrostatic capacitance sensors 80 is increased, a complicated signal processing for an output value thereof is unnecessary.

Figure 9A:
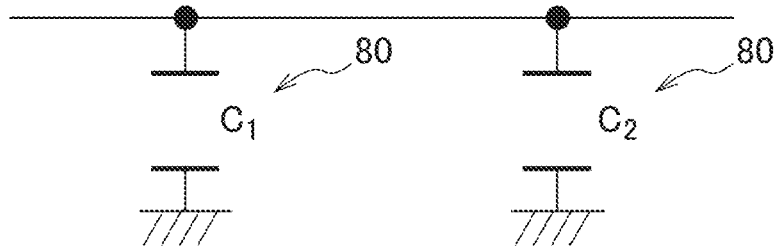
FIG. 9A is an illustrative diagram of a combined capacitance of two electrostatic capacitance sensors connected in parallel, and is an illustrative diagram showing a state where none of the electrostatic capacitance sensors detects a liquid.

As shown in FIG. 9A, for example, when two electrostatic capacitance sensors 80 are connected in parallel to the controller 50, a capacitance detected by the controller 50 (combined capacitance: $C_{sum}$) is a sum ($C_{sum}=C_1+C_2$) of capacitances ($C_1$, $C_2$) of the two electrostatic capacitance sensors 80.

Figure 9B:
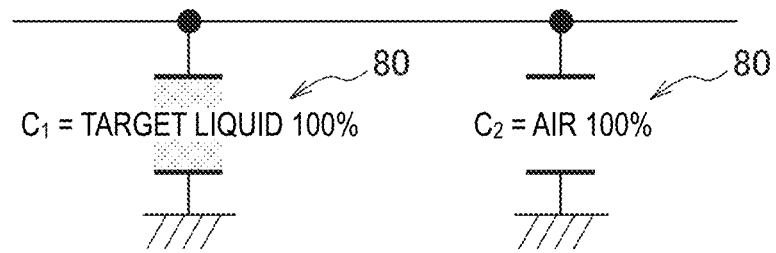
FIG. 9B is an illustrative diagram of a combined capacitance of the two electrostatic capacitance sensors connected in parallel, and is an illustrative diagram showing a state where one of the electrostatic capacitance sensors detects the liquid.

Here, as shown in FIG. 9B, when the capacitance $C_1$ of one electrostatic capacitance sensor 80 is defined by detection target liquid 100% and the capacitance $C_2$ of the other electrostatic capacitance sensor 80 is defined by air 100%, a sum ($C_{sum}=C_1+C_2$) of capacitances ($C_1$, $C_2$) of the two electrostatic capacitance sensors 80 is obtained by the following Formula (I). A state where the capacitance of the electrostatic capacitance sensor 80 is defined by the air 100% indicates a state where the electrostatic capacitance sensor 80 does not detect any detection target liquid.

$$C_{sum} = C_1 + C_2 = \frac{\varepsilon_{liquid} \cdot \varepsilon_0 \cdot S}{d} + \frac{\varepsilon_0 \cdot S}{d} = \varepsilon_0 S \frac{\varepsilon_{liquid} + 1}{d} \quad (I)$$

In Formula (I), $\varepsilon_{liquid}$ is a relative permittivity of a detection target liquid, $\varepsilon_0$ is a permittivity of air, S is an area of one parallel plate electrode, and d is a distance between plates of the parallel plate electrodes. When the electrostatic capacitance sensor 80 is configured with a pseudo capacitor including only one electrode 81, a distance between one electrode 81 and a GND potential may be used for d.

Figure 9C:
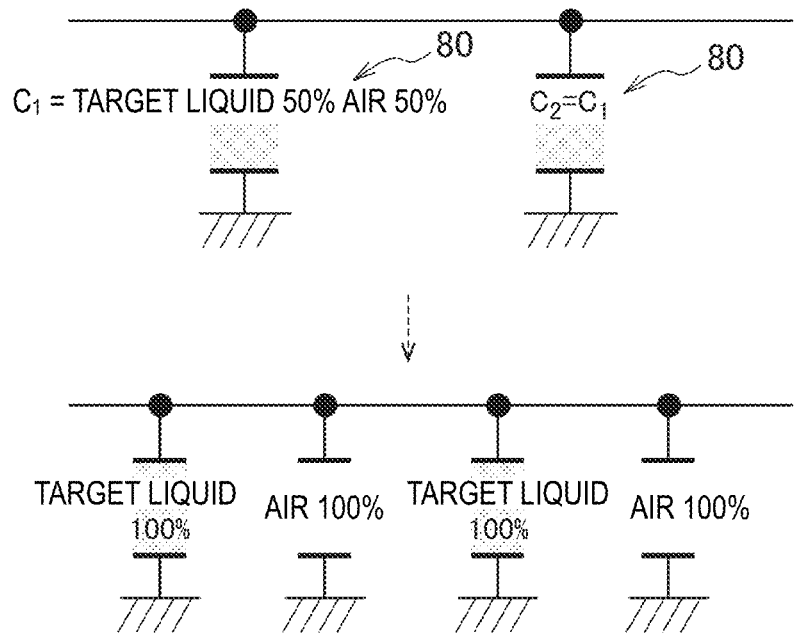
FIG. 9C is an illustrative diagram of a combined capacitance of the two electrostatic capacitance sensors connected in parallel, and is an illustrative diagram showing a state where the two electrostatic capacitance sensors detect the liquid.

As shown on an upper side of FIG. 9C, when the capacitances $C_1$ and $C_2$ of the respective electrostatic capacitance sensors 80 are equal and both of the capacitances $C_1$ and $C_2$ are defined by detection target liquid 50% and air 50%, the capacitances $C_1$ and $C_2$ of the respective electrostatic capacitance sensors 80 are replaced as shown on a lower side of FIG. 9C. In other words, in each electrostatic capacitance sensor 80, since it can be regarded that the area of the parallel plate electrode contributing to the detection target liquid and the air becomes half, a sum ($C'_{sum}=C_1+C_2$) of the capacitances ($C_1$, $C_2$) of the two electrostatic capacitance sensors 80 is obtained by the following Formula (II).

$$C'_{sum} = C_1 + C_2 = \frac{\varepsilon_{liquid} \cdot \varepsilon_0 \cdot S}{2d} + \frac{\varepsilon_0 \cdot S}{2d} + \frac{\varepsilon_{liquid} \cdot \varepsilon_0 \cdot S}{2d} + \frac{\varepsilon_0 \cdot S}{2d} = \varepsilon_0 S \frac{\varepsilon_{liquid} + 1}{d} \quad (II)$$

In Formula (II), $\varepsilon_{liquid}$ is a relative permittivity of a detection target liquid, $\varepsilon_0$ is a permittivity of air, S is an area of one parallel plate electrode, and d is a distance between plates of the parallel plate electrodes.

That is, when the two electrostatic capacitance sensors 80 are connected in parallel to the controller 50, even when a liquid amount detected by each electrostatic capacitance sensor 80 is different, when a sum of liquid amounts detected by the electrostatic capacitance sensors 80 is the same, an electrostatic capacitance detected by the controller 50 is the same. This relationship holds even when a ratio between the detection target liquid and the air of the two electrostatic capacitance sensors 80 is changed. Further, this relationship holds even when the number of the electrostatic capacitance sensors 80 connected in parallel to the controller 50 is increased.

Even when a liquid in an amount should be detected inside the power supply unit case 11 is generated due to the leakage of the liquid or the entering of the liquid, the liquid may be locally present and may diffuse in a wide range inside the power supply unit case 11. When the liquid is locally present inside the power supply unit case 11 and an electrostatic capacitance sensor 80 is provided in the vicinity of a location where the liquid is present, the liquid leakage and the like can be accurately detected with one electrostatic capacitance sensor 80.

However, when the electrostatic capacitance sensor 80 is not provided at the location where the liquid is present, a capacitance of one electrostatic capacitance sensor 80 is predominantly defined by air whose permittivity and relative permittivity are extremely small. Therefore, since the electrostatic capacitance output by one electrostatic capacitance sensor 80 has a small value, the liquid leakage and the like may not be detected by only one electrostatic capacitance sensor 80. Similarly, when the liquid diffuses in a wide range inside the power supply unit case 11, since most of the capacitance of one electrostatic capacitance sensor 80 is defined by air, the liquid leakage and the like also may not be detected by only one electrostatic capacitance sensor 80.

On the other hand, when the plurality of electrostatic capacitance sensors 80 are used, a liquid at a location that cannot be obtained by only one electrostatic capacitance sensor 80 can also be detected. Further, as long as a liquid having the same amount is detected as described above, an electrostatic capacitance detected by the controller 50 is the same regardless of a ratio of a liquid detected by the plurality of capacitance sensors 80.

When the plurality of electrostatic capacitance sensors 80 are used in this way, even when the liquid leakage and the like cannot be detected by one electrostatic capacitance sensor 80, the liquid leakage and the like can be detected by other electrostatic capacitance sensors 80. Further, even when the electrolytic solution or the like diffuses in a wide range, the liquid leakage and the like can be detected by a sum of the plurality of electrostatic capacitance sensors 80. Therefore, the state of the power supply unit 10 can be accurately diagnosed.

Specifications of the plurality of electrostatic capacitance sensors 80 may be the same. For example, the electrostatic capacitance sensors 80 are configured using the electrodes 81 of the same material, the same dimension, and the same part number. Further, dimensions and part numbers of the plurality of electrostatic capacitance sensors 80 are unified, so that the specifications of the plurality of electrostatic capacitance sensors 80 may be the same. Accordingly, a cost of the power supply unit 10 can be reduced by reducing a procurement cost. Further, an output value for a physical quantity is the same among the plurality of electrostatic capacitance sensors 80, and a processing for a plurality of output values can be simplified.

The controller 50 includes a plurality of pins for inputting sensor signals and power and outputting control signals. As shown in FIG. 5, the plurality of electrostatic capacitance sensors 80 are connected to the same pins 50a and 50b among the plurality of pins. Accordingly, since the controller 50 including a large number of pins is unnecessary, a cost and a size of the controller 50 can be reduced. Further, wiring for connecting the plurality of electrostatic capacitance sensors 80 to the controller 50 can be prevented from becoming complicated (spaghetti-like).

(Control Example)

Next, a specific control procedure of the controller 50 will be described with reference to FIGS. 10 and 11.

First, Table 1 shows typical dielectrics among dielectrics that can be present inside the aerosol suction device 1 and relative permittivities thereof.

TABLE 1

| Dielectric | Relative permittivity $\varepsilon_r$ | Application |
| --- | --- | --- |
| Ethylene carbonate (EC) | 90.0 | Electrolytic solution |
| Water | 80.4 | Aerosol source |
| Propylene carbonate (PC) | 65.0 | Electrolytic solution |
| Glycerin (G) | 47.0 | Aerosol source |
| Dimethyl sulfoxide (DMSO) | 46.7 | Electrolytic solution |
| Propylene glycol (PG) | 32.0 | Aerosol source |
| Dimethyl carbonate (DMC) | 3.1 | Electrolytic solution |
| Ethyl methyl carbonate (EMC) | 2.9 | Electrolytic solution |
| Diethyl carbonate | 2.8 | Electrolytic solution |
| Air | 1.0 | Atmospheric atmosphere |

Figure 10:
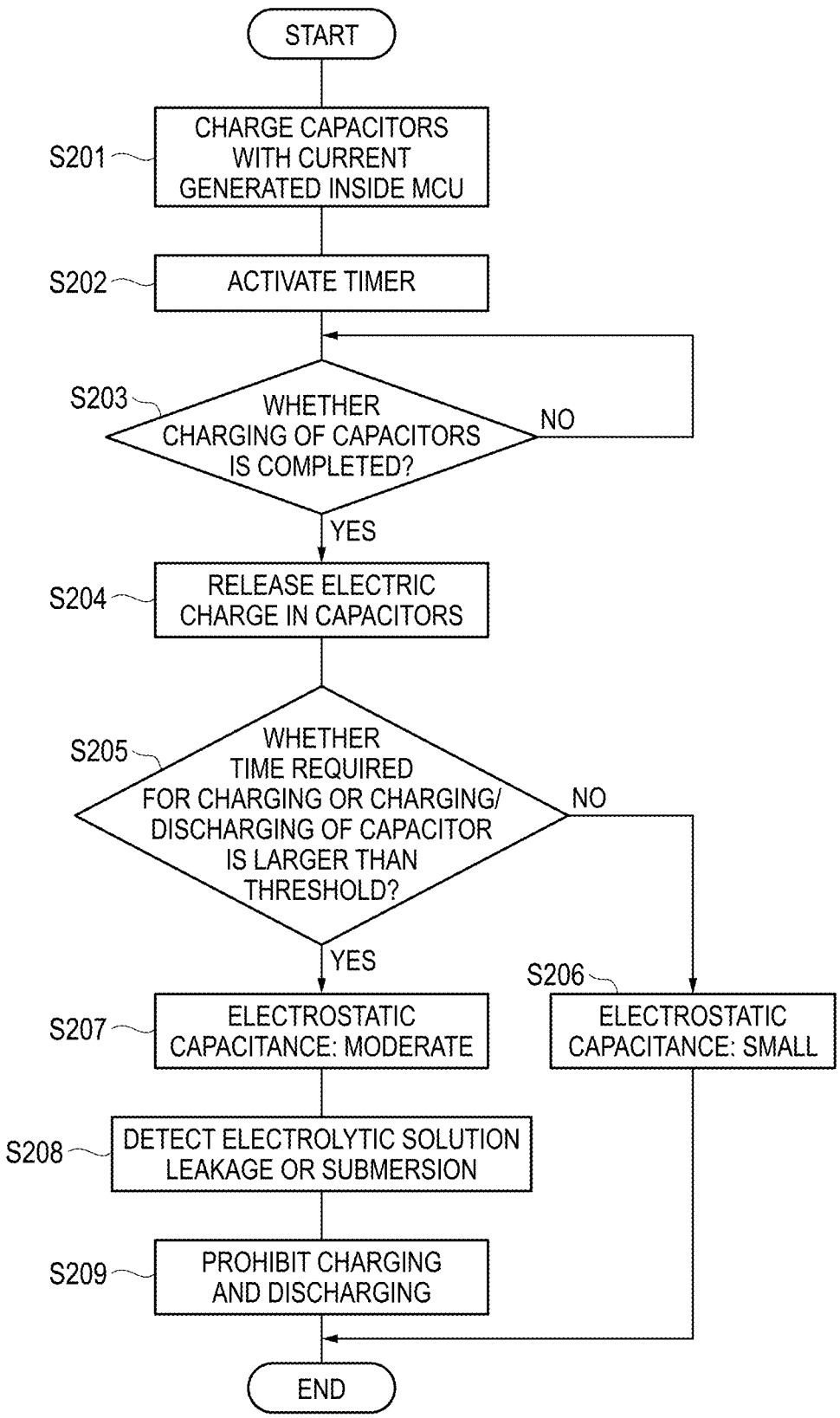
FIG. 10 is a flowchart showing a control example of the power supply unit in the aerosol suction device of FIG. 1.
Figure 11:
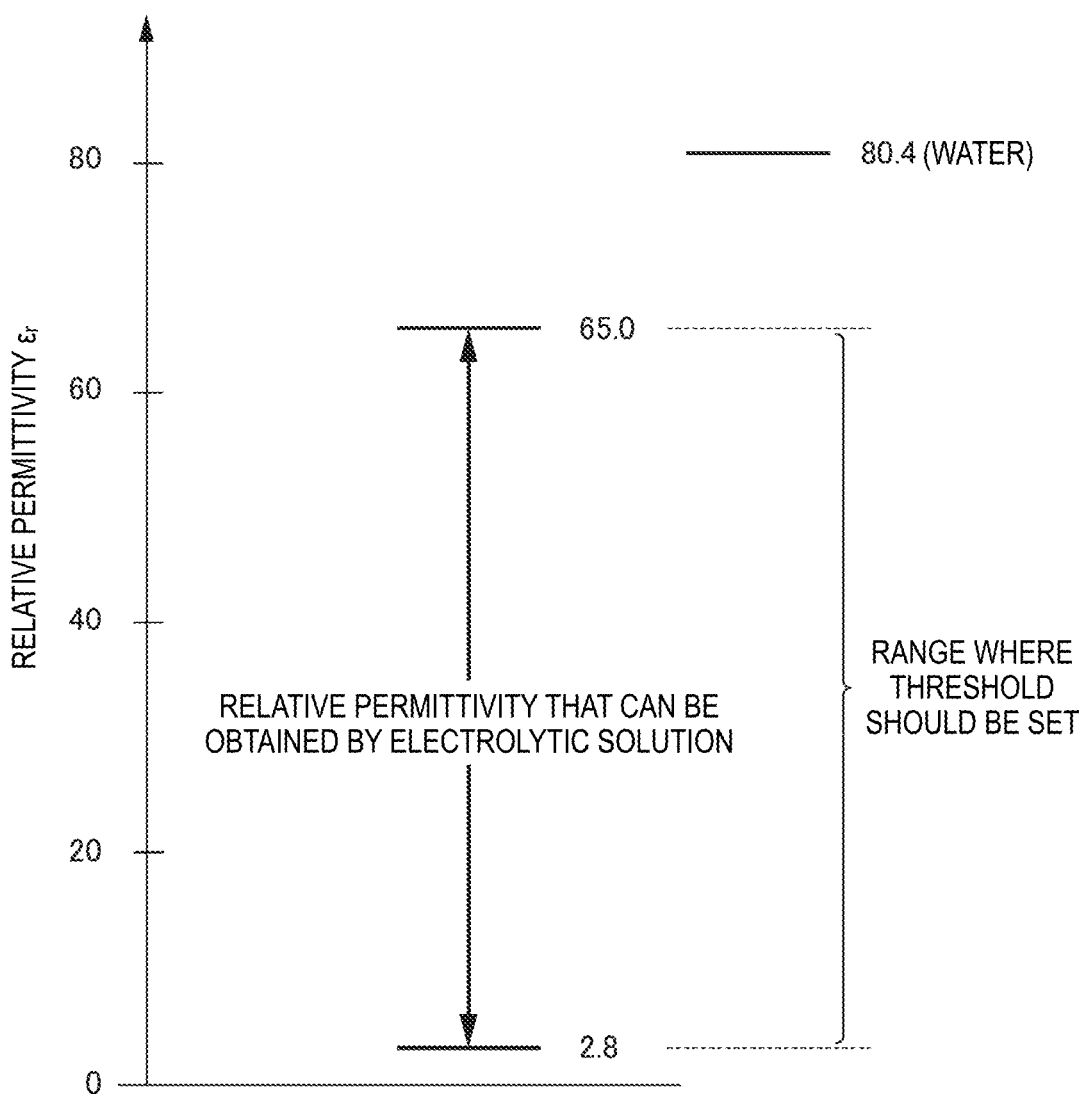
FIG. 11 is an illustrative diagram of a threshold used in the control example of FIG. 10.

In a case of a control example shown in FIG. 10, the controller 50 diagnoses an abnormality of the power supply unit 10 based on a comparison between output values of the plurality of electrostatic capacitance sensors 80 and a threshold that is based on a smaller one of a permittivity or relative permittivity of the water and a permittivity or relative permittivity of the electrolytic solution (see FIG. 11). Accordingly, since the threshold is set based on one, of the water and the electrolytic solution, that has a smaller permittivity or relative permittivity, occurrence of the abnormality can be rapidly detected without making a distinction between the electrolytic solution leakage and the submersion.

In FIG. 11, it is assumed that any one of propylene carbonate (PC), dimethyl sulfoxide (DMSO), dimethyl carbonate (DMC), ethyl methyl carbonate (EMC), and diethyl carbonate or a mixed solution thereof is used as the electrolytic solution. It is known that a relative permittivity or permittivity of the mixed solution is obtained by adding relative permittivities or permittivities of the respective solutions that constitute the mixed solution in accordance with ratios thereof. Therefore, 2.8 to 65.0 is shown as a relative permittivity that can be obtained by the electrolytic solution. Further, 80.4 is a relative permittivity that can be obtained by water at room temperature, and less than 2.8 is shown as a relative permittivity in the absence of a liquid such as an electrolytic solution or water. However, the present disclosure is not limited thereto. An obtainable value of the relative permittivity can be set in accordance with components of the electrolytic solution and the like. In the present embodiment, the threshold is set based on the electrolytic solution having a smaller relative permittivity between the water and the electrolytic solution.

A relative permittivity that can be obtained by the electrolytic solution may be obtained experimentally, or may be obtained by adding known relative permittivities of the liquids that constitute the mixed solution in accordance with a composition ratio thereof. In the following description, a permittivity may be used instead of a relative permittivity.

As shown in FIG. 10, when executing control example 2, the controller 50 first charges the capacitor (pseudo capacitor or capacitor configured by the electrostatic capacitance sensor 80) with a current generated inside the controller 50

(S201) and activates a timer (S202). Thereafter, the controller 50 repeatedly determines completion of charging of the capacitor (S203), releases electric charge accumulated in the capacitor when a determination result is YES, and obtains the time T required for charging or charging/discharging of the capacitor (S204).

Next, the controller 50 determines whether the time T is larger than the second threshold (S205). When a determination result is NO, the controller 50 determines that the electrostatic capacitance is small (S206), that is, determines that the electrolytic solution leakage and the submersion do not occur, and then ends the single detection processing. On the other hand, when YES is determined in step S205, the controller 50 determines that the electrostatic capacitance is moderate (S207), that is, determines that the electrolytic solution leakage or the submersion has been detected (S208), and prohibits a discharging processing from the power supply 12 to at least the load 21 and a charging processing of the power supply 12 (S209). The notification controller 54 may control the notification unit 45 so as to notify at the same time as step S209 or before and after step S209 that the electrolytic solution leakage has been detected. Further, the controller 50 may perform control so as to prohibit all charging and discharging processes with respect to the power supply 12 in step S209. Further, the controller 50 may perform control so as to prohibit a discharging processing from the power supply 12 to components other than the controller 50 in step S209.

As described above, in the present embodiment, the threshold may be set based on the electrolytic solution having a smaller relative permittivity between the water and the electrolytic solution. When a permittivity of the electrolytic solution and a liquid amount for determining that the electrolytic solution leakage or the submersion has been detected are known, electrostatic capacitances of the electrostatic capacitance sensors 80 during the electrolytic solution leakage or the submersion are derived based on Formula (I) and Formula (II). From the derived electrostatic capacitances, a time required for charging or charging/discharging the capacitors during the electrolytic solution leakage or the submersion may be derived, and a derived value may be used as the threshold. As another example, times required for charging or charging/discharging the capacitors during the electrolytic solution leakage and the submersion may be respectively and experimentally calculated, and a smaller value may be used as the threshold. It is apparent that the threshold set as described above is based on a smaller one of the relative permittivity or permittivity of the water and the relative permittivity or permittivity of the electrolytic solution.

In the present embodiment, in step S205, the time T is compared with the first threshold having a dimension of time. Alternatively, in step S205, the time T may be converted into a permittivity, and a converted value may be compared with a first threshold having a dimension of permittivity. Further, in step S205, the time T may be converted into a relative permittivity, and a converted value may be compared with a first threshold corresponding to the relative permittivity.

The present disclosure is not limited to the above-described embodiment, and can be appropriately modified, improved, and the like. For example, in the above-described embodiment, although the electrolytic solution leakage and the submersion are detected without distinction by using the plurality of electrostatic capacitance sensors 80, either one of the electrolytic solution leakage and the submersion may be detected using the plurality of electrostatic capacitance sensors 80. When only the electrolytic solution leakage is detected, the controller 50 can diagnose the leakage of the electrolytic solution based on a comparison between output values of the plurality of electrostatic capacitance sensors 80 and a threshold that is based on a permittivity or a relative permittivity of the electrolytic solution. When only the submersion is detected, the controller 50 can diagnose entering of the water from the openings K1 to K5 based on a comparison between the output values of the plurality of electrostatic capacitance sensors 80 and a threshold that is based on a permittivity or a relative permittivity of the water.

Further, the plurality of sensors are not limited to the electrostatic capacitance sensors 80 as long as the plurality of sensors are sensors that can output the same physical quantity inside the power supply unit case 11. For example, the plurality of sensors may be sensors that can detect a bulge of the power supply 12. The controller 50 may be configured to diagnose the bulge of the power supply 12 based on outputs of the plurality of sensors. Accordingly, the abnormal bulge of the power supply 12 can be rapidly detected. As a sensor that can detect the bulge of the power supply 12, a pressure sensor, a strain gauge, or the like may be used.

At least the following matters are described in the present description. Components corresponding to the above-described embodiments are shown in parentheses, but the present disclosure is not limited thereto.

(1)

A power supply unit (power supply unit 10) of an aerosol generation apparatus (aerosol suction device 1), including:

a power supply (power supply 12) capable of discharging to a load (load 21) for generating an aerosol from an aerosol source;

a controller (controller 50) configured to control the power supply; and a housing (power supply unit case 11) configured to house the power supply and the controller, in which a plurality of sensors (electrostatic capacitance sensor 80) capable of outputting the same physical quantity inside the housing, wherein the controller is configured to diagnose a state of the power supply unit based on outputs of the plurality of sensors.

According to (1), the controller diagnoses the state of the power supply unit based on the outputs of the plurality of sensors that can output the same physical quantity inside the housing. Therefore, diagnostic accuracy and diagnostic speed of the state of the power supply unit are improved.

(2)

The power supply unit of the aerosol generation apparatus according to (1), in which The power supply unit of the aerosol generation apparatus according to claim 1, wherein the plurality of sensors are connected in parallel to each other.

According to (2), since the plurality of sensors are connected in parallel to each other, wiring can be simplified. Further, the wiring can be reduced.

(3)

The power supply unit of the aerosol generation apparatus according to (1) or (2), in which the controller is configured to diagnose the state of the power supply unit based on a sum of output values of the plurality of sensors.

According to (3), since the controller diagnoses the state of the power supply unit based on the sum of the output values of the plurality of sensors, a processing for a plurality of output values can be simplified.

(4)

The power supply unit of the aerosol generation apparatus according to any one of (1) to (3), in which specifications of the plurality of sensors are the same.

According to (4), since the specifications of the plurality of sensors are the same, a cost of the power supply unit can be reduced by reducing a procurement cost. Further, an output value for a physical quantity is the same among the plurality of sensors, and a processing for the plurality of output values can be simplified.

(5)

The power supply unit of the aerosol generation apparatus according to any one of (1) to (4), in which the controller has a plurality of pins, and the plurality of sensors are connected to the same pins among the plurality of pins (pins 50*a*, 50*b*).

According to (5), since the plurality of sensors are connected to the same pins among the plurality of pins of the controller, the controller including a large number of pins is unnecessary, and thus a cost and a size of the controller can be reduced. Further, wiring for connecting the plurality of sensors to the controller can be prevented from becoming complicated (spaghetti-like).

(6)

The power supply unit of the aerosol generation apparatus according to any one of (1) to (5), in which the plurality of sensors are a plurality of electrostatic capacitance sensors (electrostatic capacitance sensors 80), and the controller is configured to diagnose, based on outputs of the plurality of electrostatic capacitance sensors, at least one of leakage of a liquid inside the housing and entering of a liquid into the housing.

According to (6), the controller can diagnose, based on the outputs of the plurality of electrostatic capacitance sensors, at least one of the leakage of the liquid inside the housing and the entering of the liquid into the housing. Therefore, occurrence of electrolytic solution leakage, submersion, and the like of the power supply can be rapidly detected.

(7)

The power supply unit of the aerosol generation apparatus according to (6), in which the plurality of electrostatic capacitance sensors include at least a first electrostatic capacitance sensor and a second electrostatic capacitance sensor, the first electrostatic capacitance sensor is connected to a safety valve or a tab (12*b*) that are provided in the power supply or is disposed in a vicinity of the safety valve or the tab, and the second electrostatic capacitance sensor is connected to an opening (openings K1 to K5) provided in the housing or is disposed in a vicinity of the opening.

According to (7), since the electrostatic capacitance sensors are respectively connected to or arranged at locations where the electrolytic solution leakage and the submersion easily occur, occurrence of the electrolytic solution leakage and the submersion can be rapidly detected.

(8)

The power supply unit of the aerosol generation apparatus according to (7), in which the power supply includes an electrolytic solution, and the controller is configured to diagnose an abnormality of the power supply unit based on the output values of the plurality of electrostatic capacitance sensors and a smaller one of a permittivity or a relative permittivity of water and a permittivity or a relative permittivity of the electrolytic solution.

According to (8), since the threshold is set based on one, of the water and the electrolytic solution, that has a smaller permittivity or relative permittivity, occurrence of the abnormality can be rapidly detected without making a distinction between the electrolytic solution leakage and the submersion.

(9)

The power supply unit of the aerosol generation apparatus according to (6), in which at least one of the plurality of electrostatic capacitance sensors is connected to a safety valve or a tab (tab 12*b*) that are provided in the power supply or is disposed in a vicinity of the safety valve or the tab.

According to (9), since at least one of the plurality of electrostatic capacitance sensors is connected to or disposed at a location where the electrolytic solution leakage easily occurs, occurrence of the electrolytic solution leakage can be rapidly detected.

(10)

The power supply unit of the aerosol generation apparatus according to (9), in which the power supply includes an electrolytic solution, and the controller is configured to diagnose leakage of the electrolytic solution as the leakage, based on a comparison between output values of the plurality of electrostatic capacitance sensors and a threshold that is based on a permittivity or a relative permittivity of the electrolytic solution.

According to (10), since the threshold is set based on the permittivity or the relative permittivity of the electrolytic solution, occurrence of the electrolytic solution leakage can be rapidly detected.

(11)

The power supply unit of the aerosol generation apparatus according to (6), wherein at least one of the plurality of electrostatic capacitance sensors is connected to an opening (openings K1 to K5) provided in the housing or is disposed in a vicinity of the opening.

According to (11), since at least one of the plurality of electrostatic capacitance sensors is connected to or disposed at a location where the submersion easily occurs, occurrence of the submersion can be rapidly detected.

(12)

The power supply unit of the aerosol generation apparatus according to (11), in which the controller is configured to diagnose entering of water from the opening as the entering, based on a comparison between output values of the plurality of electrostatic capacitance sensors and a threshold that is based on a permittivity or a relative permittivity of the water.

According to (12), since the threshold is set based on the permittivity or the relative permittivity of the water, occurrence of the submersion can be rapidly detected.

(13)

The power supply unit of the aerosol generation apparatus according to any one of (7), (9), and (11), in which each electrostatic capacitance sensor is connected via a porous body (first porous body 82) configured to guide the liquid to the electrostatic capacitance sensor.

According to (13), the electrostatic capacitance sensor is connected to, via the porous body that guides the liquid to the electrostatic capacitance sensor, a location where the electrolytic solution leakage or the submersion easily occurs. Therefore, there is a high degree of freedom in an arrangement position of the electrostatic capacitance sensor. Therefore, the power supply unit 10 can be downsized.

(14)

The power supply unit of the aerosol generation apparatus according to any one of (1) to (5), in which the plurality of sensors are sensors configured to detect a bulge of the power supply, and the controller is configured to diagnose the bulge of the power supply based on the outputs of the plurality of sensors.

According to (14), since the controller is configured to diagnose the bulge of the power supply based on the outputs of the plurality of sensors, an abnormal cell bulge can be rapidly detected.

The invention claimed is:

1. A power supply unit of an aerosol generation apparatus, comprising:
 a power supply capable of discharging to a load for generating an aerosol from an aerosol source;
 a controller configured to control the power supply;
 a housing configured to house the power supply and the controller; and
 a plurality of electrostatic capacitance sensors, wherein
 the controller is configured to diagnose, based on outputs of the plurality of electrostatic capacitance sensors, at least one of abnormal leakage of a liquid inside the housing and entering of a liquid into the housing.

2. The power supply unit of the aerosol generation apparatus according to claim 1, wherein
 the plurality of electrostatic capacitance sensors are connected in parallel to each other.

3. The power supply unit of the aerosol generation apparatus according to claim 1, wherein
 the controller is configured to diagnose, based on a sum of output values of the plurality of electrostatic capacitance sensors, at least one of the abnormal leakage and the entering.

4. The power supply unit of the aerosol generation apparatus according to claim 1, wherein
 specifications of the plurality of electrostatic capacitance sensors are the same.

5. The power supply unit of the aerosol generation apparatus according to claim 1, wherein
 the controller has a plurality of pins, and
 the plurality of electrostatic capacitance sensors are connected to the same pins among the plurality of pins.

6. The power supply unit of the aerosol generation apparatus according to claim 1, wherein
 the plurality of electrostatic capacitance sensors include at least a first electrostatic capacitance sensor and a second electrostatic capacitance sensor,
 the first electrostatic capacitance sensor is connected to a safety valve or a tab that are provided in the power supply or is disposed in a vicinity of the safety valve or the tab, and
 the second electrostatic capacitance sensor is connected to an opening provided in the housing or is disposed in a vicinity of the opening.

7. The power supply unit of the aerosol generation apparatus according to claim 6, wherein
 the power supply includes an electrolytic solution, and
 the controller is configured to diagnose at least one of the abnormal leakage and the entering based on output values of the plurality of electrostatic capacitance sensors and a smaller one of a permittivity or a relative permittivity of water and a permittivity or a relative permittivity of the electrolytic solution.

8. The power supply unit of the aerosol generation apparatus according to claim 1, wherein
 at least one of the plurality of electrostatic capacitance sensors is connected to a safety valve or a tab that are provided in the power supply or is disposed in a vicinity of the safety valve or the tab.

9. The power supply unit of the aerosol generation apparatus according to claim 8, wherein
 the power supply includes an electrolytic solution, and
 the controller is configured to diagnose leakage of the electrolytic solution as the abnormal leakage, based on a comparison between output values of the plurality of electrostatic capacitance sensors and a threshold that is based on a permittivity or a relative permittivity of the electrolytic solution.

10. The power supply unit of the aerosol generation apparatus according to claim 1, wherein
 at least one of the plurality of electrostatic capacitance sensors is connected to an opening provided in the housing or is disposed in a vicinity of the opening.

11. The power supply unit of the aerosol generation apparatus according to claim 10, wherein
 the controller is configured to diagnose entering of water from the opening as the entering, based on a comparison between output values of the plurality of electrostatic capacitance sensors and a threshold that is based on a permittivity or a relative permittivity of the water.

12. The power supply unit of the aerosol generation apparatus according to claim 6, wherein
 each electrostatic capacitance sensor is connected via a porous body configured to guide the liquid to the electrostatic capacitance sensor.

13. An apparatus comprising:
 a power supply configured to discharge to a load for generating an aerosol from an aerosol source;
 a controller configured to control the power supply;
 a housing configured to house the power supply and the controller; and
 a plurality of electrostatic capacitance sensors, wherein
 the controller is configured to
  diagnose, based on outputs of the plurality of electrostatic capacitance sensors, at least one of leakage of a liquid inside the housing and entering of a liquid into the housing; and
  control the power supply not to discharge to the load in a case of diagnosing the at least one of the leakage of liquid inside the housing and entering of a liquid into the housing.

14. The apparatus of claim 13, wherein
 at least one of the plurality of electrostatic capacitance sensors is connected to a safety valve or a tab that are provided in the power supply or is disposed in a vicinity of the safety valve or the tab.

15. The apparatus of claim 13, wherein
 at least one of the plurality of electrostatic capacitance sensors is connected to an opening provided in the housing or is disposed in a vicinity of the opening.

16. The apparatus of claim 15, wherein
 the controller is configured to diagnose entering of water from the opening as the entering.

17. The apparatus of claim 15, wherein
 the controller is configured to diagnose entering of water from the opening as the entering, based on a comparison between output values of the plurality of electrostatic capacitance sensors and a threshold that is based on a permittivity or a relative permittivity of the water.

18. The apparatus of claim 13, wherein each electrostatic capacitance sensor is connected via a porous body configured to guide the liquid to the electrostatic capacitance sensor.

19. The apparatus of claim 13, wherein the power supply includes an electrolytic solution, and the controller is configured to diagnose leakage of the electrolytic solution as the leakage.

20. An apparatus comprising:
a power supply configured to discharge to a load for generating an aerosol from an aerosol source;
a controller configured to control the power supply;

a housing configured to house the power supply and the controller; and a plurality of electrostatic capacitance sensors, wherein the controller is configured to diagnose, based on outputs of the plurality of electrostatic capacitance sensors, at least one of leakage of a liquid inside the housing and entering of a liquid into the housing, and at least one of the plurality of electrostatic capacitance sensors is connected to a safety valve or a tab that are provided in the power supply or is disposed in a vicinity of the safety valve or the tab.

* * * * *